(12) United States Patent  
Melsheimer et al.

(10) Patent No.: US 7,303,572 B2
(45) Date of Patent: Dec. 4, 2007

(54) CATHETER ASSEMBLY WITH PLAQUE CUTTING BALLOON

(75) Inventors: Jeffry S. Melsheimer, Springville, IN (US); David G. Burton, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 11/319,974

(22) Filed: Dec. 28, 2005

(65) Prior Publication Data

US 2006/0149308 A1    Jul. 6, 2006

Related U.S. Application Data

(60) Provisional application No. 60/640,779, filed on Dec. 30, 2004.

(51) Int. Cl.
A61B 17/22 (2006.01)
A61B 17/32 (2006.01)
B26B 29/00 (2006.01)

(52) U.S. Cl. .................. 606/159; 606/170; 30/287
(58) Field of Classification Search ................ 606/159
See application file for complete search history.

(56) References Cited

U.S. PATENT DOCUMENTS

| | | | |
|---|---|---|---|
| 4,535,757 A | 8/1985 | Webster, Jr. | |
| 4,729,763 A | 3/1988 | Henrie | |
| 4,877,030 A | 10/1989 | Beck et al. | |
| 4,886,061 A | 12/1989 | Fischell et al. | |
| 4,898,575 A | 2/1990 | Fischell et al. | |
| 4,983,167 A | 1/1991 | Sahota | |
| 5,009,659 A * | 4/1991 | Hamlin et al. | 606/159 |
| 5,019,042 A | 5/1991 | Sahota | |
| 5,030,201 A | 7/1991 | Palestrant | |
| 5,047,040 A | 9/1991 | Simpson et al. | |
| 5,057,120 A | 10/1991 | Farcot | |
| 5,078,723 A | 1/1992 | Dance et al. | |
| 5,080,660 A | 1/1992 | Buelna | |
| 5,090,958 A | 2/1992 | Sahota | |
| 5,147,377 A | 9/1992 | Sahota | |
| 5,160,321 A | 11/1992 | Sahota | |
| 5,181,920 A | 1/1993 | Mueller et al. | |
| 5,192,291 A | 3/1993 | Pannek, Jr. | |

(Continued)

FOREIGN PATENT DOCUMENTS

EP    0 117 519 A1    9/1984

(Continued)

Primary Examiner—Michael J. Hayes
Assistant Examiner—Katherine Dowe
(74) Attorney, Agent, or Firm—Brinks Hofer Gilson & Lione (57) ABSTRACT

A balloon catheter assembly comprises an elongate catheter shaft having a proximal portion and a distal portion, and an inflatable balloon secured to the shaft distal portion. A plurality of cutters are arranged along an outer surface of the balloon. The cutters are shielded by folds of the balloon when the balloon is uninflated, and are arranged and configured to facilitate breakdown of a vascular restriction when said balloon is inflated. Preferably, the cutters are arranged in at least three generally parallel longitudinal rows along the balloon outer surface, and there are at least three longitudinally-aligned cutters in each row. Preferably, the cutters are formed of the same or a similar base composition as the balloon, and are bonded to the balloon outer surface.

19 Claims, 5 Drawing Sheets

U.S. PATENT DOCUMENTS

| | | | |
|---|---|---|---|
| 5,196,024 A | 3/1993 | Barath | |
| 5,209,749 A | 5/1993 | Buelna | |
| 5,224,945 A | 7/1993 | Pannek, Jr. | |
| 5,224,949 A | 7/1993 | Gomringer et al. | |
| 5,320,605 A | 6/1994 | Sahota | |
| 5,320,634 A | 6/1994 | Vigil et al. | |
| 5,336,178 A | 8/1994 | Kaplan et al. | |
| 5,336,234 A * | 8/1994 | Vigil et al. | 606/159 |
| 5,372,601 A | 12/1994 | Lary | |
| 5,395,332 A | 3/1995 | Ressemann et al. | |
| 5,409,454 A | 4/1995 | Fischell et al. | |
| 5,411,478 A | 5/1995 | Stillabower | |
| 5,431,673 A | 7/1995 | Summers et al. | |
| 5,441,510 A | 8/1995 | Simpson et al. | |
| 5,450,843 A | 9/1995 | Moll et al. | |
| 5,505,725 A | 4/1996 | Samson | |
| 5,522,790 A | 6/1996 | Moll et al. | |
| 5,556,408 A | 9/1996 | Farhat | |
| 5,569,277 A | 10/1996 | Evans et al. | |
| 5,571,087 A | 11/1996 | Ressemann et al. | |
| 5,575,771 A | 11/1996 | Walinsky | |
| 5,609,628 A | 3/1997 | Keranen | |
| 5,616,149 A * | 4/1997 | Barath | 606/159 |
| 5,628,746 A | 5/1997 | Clayman | |
| 5,722,979 A | 3/1998 | Kusleika | |
| 5,728,129 A | 3/1998 | Summers | |
| 5,779,698 A | 7/1998 | Clayman et al. | |
| 5,792,158 A | 8/1998 | Lary | |
| 5,797,935 A | 8/1998 | Barath | |
| 5,904,679 A | 5/1999 | Clayman | |
| 5,910,144 A | 6/1999 | Hayashi | |
| 5,921,958 A | 7/1999 | Ressemann et al. | |
| 5,941,869 A | 8/1999 | Patterson et al. | |
| 6,036,689 A | 3/2000 | Tu et al. | |
| 6,036,708 A | 3/2000 | Sciver | |
| 6,071,285 A | 6/2000 | Lashinski et al. | |
| 6,123,718 A | 9/2000 | Tu et al. | |
| 6,165,187 A | 12/2000 | Reger | |
| 6,231,572 B1 | 5/2001 | Hart et al. | |
| 6,245,040 B1 | 6/2001 | Inderbitzen et al. | |
| 6,254,608 B1 | 7/2001 | Solar | |
| 6,280,464 B1 | 8/2001 | Hayashi | |
| 6,283,947 B1 | 9/2001 | Mirzaee | |
| 6,306,151 B1 | 10/2001 | Lary | |
| 6,319,242 B1 * | 11/2001 | Patterson et al. | 604/508 |
| 6,355,013 B1 | 3/2002 | van Muiden | |
| 6,500,186 B2 | 12/2002 | Lafontaine et al. | |
| 6,508,824 B1 | 1/2003 | Flaherty et al. | |
| 6,629,953 B1 | 10/2003 | Boyd | |
| 6,632,231 B2 * | 10/2003 | Radisch, Jr. | 606/159 |
| 6,746,463 B1 | 6/2004 | Schwartz | |
| 6,808,531 B2 | 10/2004 | Lafontaine et al. | |
| 6,885,124 B2 | 4/2005 | Neet | |
| 7,070,576 B2 * | 7/2006 | O'Brien et al. | 604/96.01 |
| 2001/0051810 A1 | 12/2001 | Dubrul et al. | |
| 2003/0028212 A1 | 2/2003 | Saab | |
| 2003/0040754 A1 | 2/2003 | Mitchell et al. | |
| 2003/0114868 A1 | 6/2003 | Fischell et al. | |
| 2003/0114877 A1 | 6/2003 | Gellman | |
| 2003/0144677 A1 | 7/2003 | Lary | |
| 2003/0229370 A1 | 12/2003 | Miller | |
| 2004/0111108 A1 | 6/2004 | Farnan | |
| 2004/0122465 A1 | 6/2004 | McMurtry et al. | |
| 2004/0127920 A1 | 7/2004 | Radisch, Jr. | |
| 2004/0143287 A1 | 7/2004 | Konstantino et al. | |
| 2004/0193196 A1 | 9/2004 | Appling et al. | |
| 2004/0199191 A1 | 10/2004 | Schwartz | |
| 2004/0230178 A1 | 11/2004 | Wu | |
| 2004/0243158 A1 | 12/2004 | Konstantino et al. | |
| 2005/0021070 A1 | 1/2005 | Feld et al. | |
| 2005/0021071 A1 | 1/2005 | Konstantino et al. | |
| 2005/0033334 A1 | 2/2005 | Santra et al. | |
| 2005/0090845 A1 | 4/2005 | Boyd | |
| 2005/0090846 A1 | 4/2005 | Pedersen et al. | |

FOREIGN PATENT DOCUMENTS

| | | |
|---|---|---|
| WO | WO 2004/060460 A2 | 7/2004 |
| WO | WO 2004060460 A2 * | 7/2004 |

* cited by examiner

CATHETER ASSEMBLY WITH PLAQUE CUTTING BALLOON

RELATED APPLICATIONS

The present patent document claims the benefit of the filing date under 35 U.S.C. §119(e) of Provisional U.S. patent application Ser. No. 60/640,779, filed Dec. 30, 2004, which is hereby incorporated by reference.

BACKGROUND

1. Technical Field

The present invention relates generally to balloon catheters, and more particularly, to a balloon catheter assembly for use in angioplasty procedures wherein the balloon portion of the assembly is provided with plaque-cutting edges disposed along the outer surface of the balloon.

2. Background Information

Coronary artery disease, or atherosclerosis, results in restrictions in the flow of blood to the heart and other areas of the circulatory system. Such restrictions occur primarily as a result of the formation of obstructions, such as plaque, in one or more of the blood vessels of the patient.

The medical community has long sought effective ways to remove such obstructions to restore the free blood flow in the vessel, and to maintain that flow for an extended period of time. One technique that has come into widespread use for treating atherosclerosis is known as percutaneous transluminal coronary angioplasty (PTCA), or as it is more commonly known, balloon angioplasty. Balloon angioplasty is utilized to open arteries whose lumens have been restricted due to this build-up of plaque, a condition known as stenosis. In a typical balloon angioplasty procedure, an incision is made in a specific area of the patient's body to gain access to an artery, such as the femoral artery. A balloon-tipped catheter is inserted into the artery and threaded through the artery to the site of the blockage. When the blockage site is reached, the balloon is inflated. The inflated balloon pushes the plaque back against the artery wall, thereby removing the restriction and restoring the pathway for blood flow through the vessel. The balloon may be deflated and re-inflated one or more additional times. If desired, a stent may be inserted at the position of the blockage to prop the artery open.

Balloon angioplasty has been well-received in the medical field as an alternative for the much more invasive and expensive surgical by-pass techniques. Although balloon angioplasty and related procedures have proven successful in many cases for treating coronary artery disease, the procedure continues to suffer from some shortcomings. Since the plaque is pressed against the vessel wall, it is not generally removed from the vessel. In a significant number of patients, the plaque re-forms as a restriction and re-clogs the artery, a condition referred to as restenosis. When restenosis occurs, it is often necessary to repeat the balloon angioplasty procedure, or in some instances, undertake a more invasive procedure, such as cardiac by-pass surgery.

In addition, in some severe cases of stenosis, the plaque deposit may have hardened or become calcified to such an extent that it does not easily yield to the balloon. In such instances, balloon angioplasty must often be carried out at higher pressures to crack the calcified plaque. When higher pressures are employed, the physician must exercise a high amount of care to avoid rupturing the balloon and/or the artery at the site of the plaque deposit.

It is desired to provide a balloon angioplasty device that is capable of breaking down build-ups of plaque from a vessel, and that is capable of cracking calcified plaque at low pressures such that the inherent risks of rupture of the balloon and/or artery may be minimized.

BRIEF SUMMARY

The problems of the prior art are addressed by the balloon catheter assembly of the present invention. The inventive balloon catheter assembly is structured such that the balloon portion of the assembly concentrates forces at cutters placed at discrete locations along the surface of the balloon. As a result, the device is effective in cracking calcified lesions, while at the same time reducing the need for higher pressures to expand the vessel.

In one form thereof, the invention comprises a balloon catheter assembly for use in breaking down restrictions in a blood vessel. The assembly comprises an elongated catheter shaft having a proximal portion and a distal portion, and an inflatable balloon secured to the shaft distal portion. A plurality of cutters is disposed along an outer surface of the balloon. The cutters are shielded by folds of the balloon when the balloon is in an uninflated condition, and are arranged and configured to facilitate breakdown of a vascular restriction when the balloon is in an inflated condition.

In another form thereof, the invention comprises a method for breaking down a restriction in a blood vessel of a patient. A balloon catheter assembly is provided for insertion into the vessel. The balloon catheter assembly comprises an elongate catheter shaft and an inflatable balloon secured to a distal portion of the catheter shaft. The balloon has a plurality of cutters fixedly disposed in respective generally parallel longitudinal rows along an outer surface thereof. The cutters are shielded by folds of the balloon when the balloon is in an uninflated condition, and are arranged and configured to facilitate a breakdown of the restriction when the balloon is in an inflated condition. The distal end of the balloon catheter assembly is inserted into the vessel, and advanced in the vessel with the balloon in an uninflated condition until the uninflated balloon reaches the restriction. The balloon is then inflated such that the cutters penetrate the restriction. The balloon is then deflated. The balloon may be reinflated and deflated additional times if desired.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the balloon catheter assembly, as well as the axial ends of various component features. The term "proximal" is used in its conventional sense to refer to the end of the assembly, or component thereof, that is closest to the operator during use of the assembly. The term "distal" is used in its conventional sense to refer to the end of the assembly, or component thereof, that is initially inserted into the patient, or that is closest to the patient.

Figure 1:
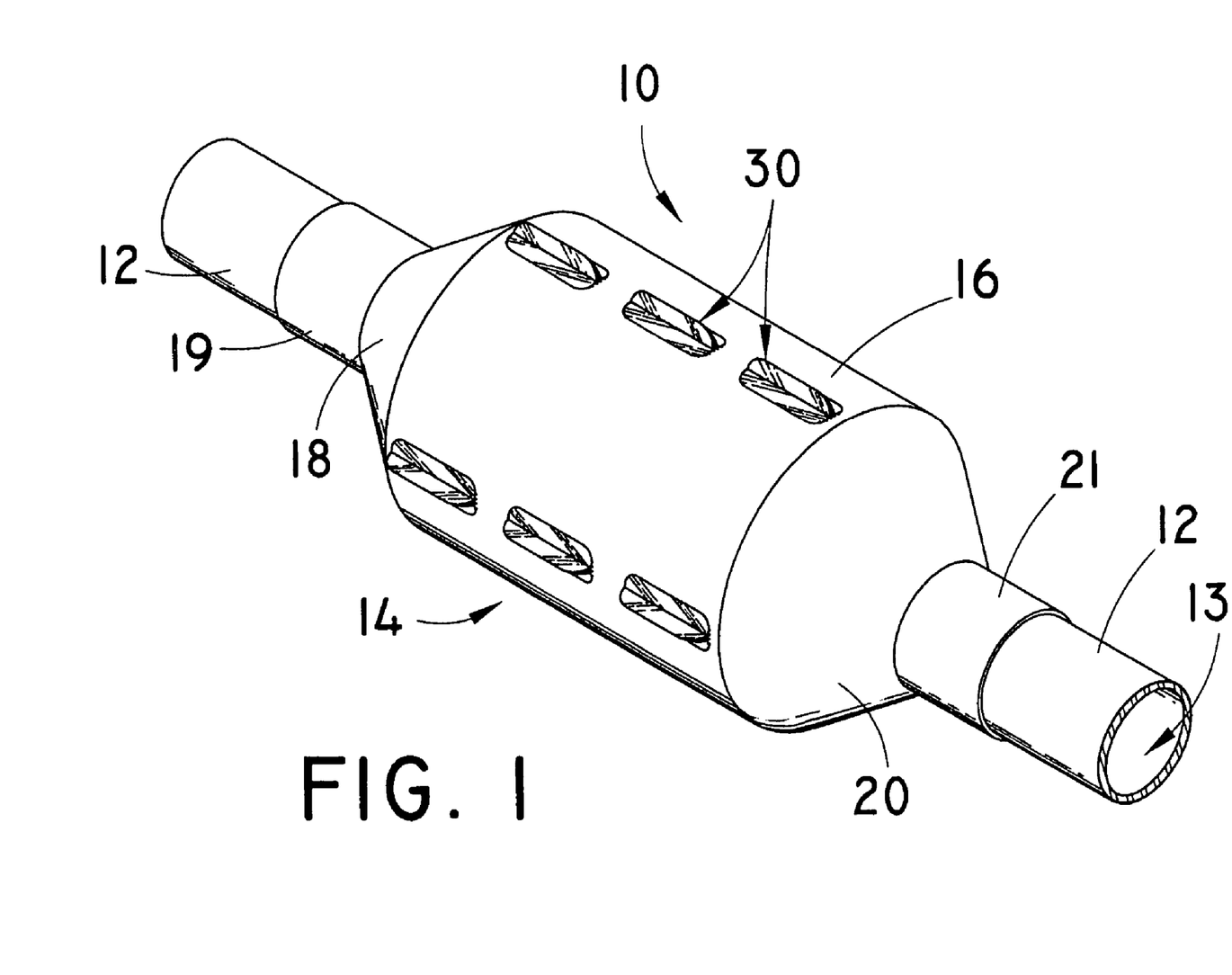
FIG. 1 is a perspective view of a distal portion of a balloon catheter according to an embodiment of the present invention, showing the balloon in an inflated condition.
Figure 2:
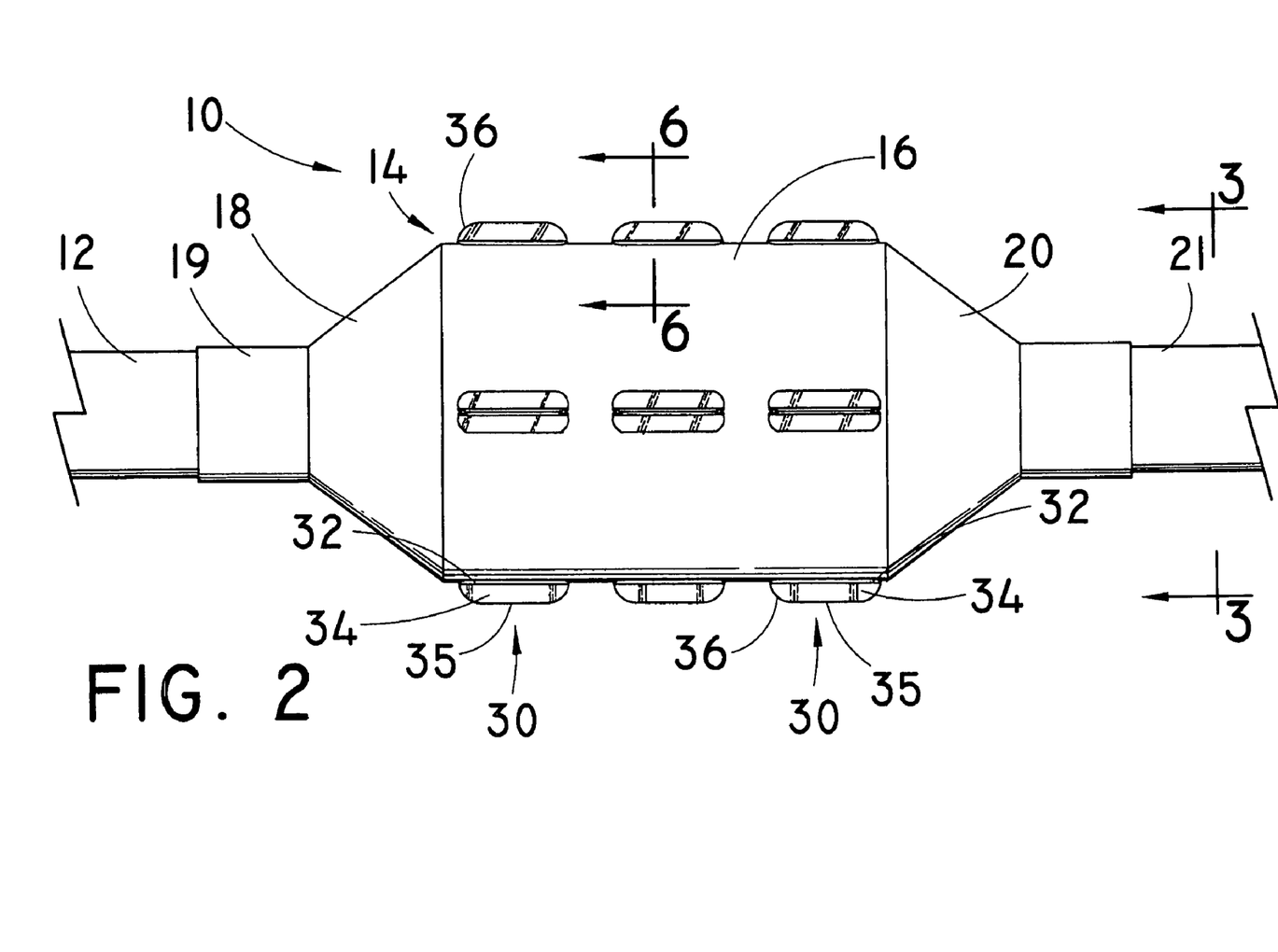
FIG. 2 is a side view of the balloon catheter portion shown in FIG. 1.
Figure 3:
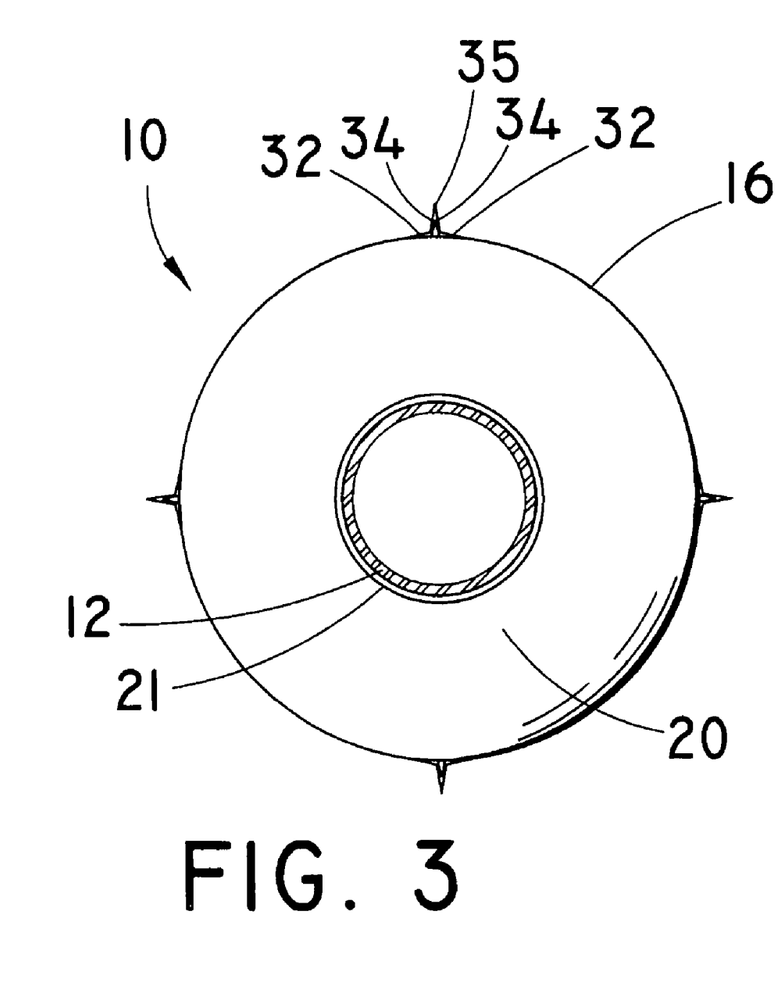
FIG. 3 is a distal end view of the catheter of FIG. 2 taken from line 3-3 of FIG. 2.

FIG. 1 illustrates a perspective view of the distal portion of a balloon catheter assembly 10 according to an embodiment of the present invention. FIG. 2 illustrates a side view of the balloon catheter assembly of FIG. 1, and FIG. 3 illustrates an end view, as viewed from the distal end of the assembly portion shown in FIG. 2. The portion of balloon catheter assembly 10 shown in FIGS. 1-3 includes a conventional catheter shaft 12 having a lumen 13 and an expandable balloon 14. The balloon is shown in its inflated condition in each of FIGS. 1-3. Other conventional features of a balloon catheter assembly are not germane to the features of the present invention, and have been omitted from these figures.

Balloon 14 comprises a generally cylindrical outer main body 16, and includes a proximal taper 18 and a distal taper 20. Proximal taper 18 tapers to proximal balloon end portion 19, and distal taper 20 tapers to distal balloon end portion 21. Respective proximal and distal end portions 19, 21 are sealingly engaged with catheter shaft 12 to provide a fluid tight connection between the catheter shaft and the respective proximal and distal ends of the balloon in well-known fashion. Balloon may be inflated in conventional fashion, such as by passing an inflation fluid from an inflation source through a lumen in catheter shaft 12, and into the interior space of the balloon through one or more ports in the shaft.

Preferably, balloon 14 is a non-compliant balloon of the type commonly used in balloon angioplasty procedures. Such balloons are well-known in the art, and are typically extruded from polymeric materials such as various polyamides (e.g., nylons), polyethylene terephthalate (PET), polyether block amides (PEBA), and mixtures of the foregoing. Non-compliant balloons are well-known for their ability to maintain their inflated diameter under high pressure conditions of the type that may be encountered during a balloon angioplasty procedure. Although non-compliant balloons are preferred for this reason, those skilled in the art will appreciate that compliant balloons may be acceptable in some circumstances when it is expected that less severe conditions will be encountered. Nevertheless, it is believed that the use of a non-compliant balloon is generally superior to a compliant balloon in most cases, and its use is therefore preferred. Angioplasty balloons are well known, and those skilled in the art can readily select an appropriate balloon for use in carrying out a particular angioplasty procedure.

As shown in FIGS. 1-3, balloon 14 is provided with a plurality of cutters 30 distributed along the outer surface of the balloon. Cutters 30 are preferably formed from a polymer. In a particularly preferred embodiment, cutters 30 are formed from the same base polymer that is used to form balloon 14, or from a base polymer having a similar composition as that of the base polymer. Cutters 30 should, of course, have sufficient strength and rigidity to break down vascular restrictions encountered upon the introduction of the balloon into a body vessel, as discussed hereinafter.

Cutters 30 are arranged along the outer surface of balloon 14 in a manner that that enables the cutters to break down vascular restrictions. Such restrictions commonly comprise arterial plaque, although in more severe cases the restrictions may comprise hardened calcified lesions in the blood vessel. In a preferred embodiment, the cutters are arranged in the manner shown in the figures. That is, there are four substantially equally-spaced rows of cutters. The four rows of cutters are disposed parallel to the longitudinal axis of the balloon catheter assembly 10, and are equally spaced approximately 90° apart along the outer circumference of the balloon. Each row of cutters preferably includes a plurality of individual cutters 30 arranged in a longitudinal row as shown.

The configuration shown in the drawings and described herein is exemplary only, and those skilled in the art will appreciate that more, or fewer, rows of cutters may be provided. In addition, the rows need not necessarily be equally spaced along the outer circumference of the balloon. Similarly, each row need not include three cutters as shown in the figures, and may include more, or fewer cutters.

Preferably, each row will include a plurality of discrete cutters as shown, rather than a single elongated cutter that spans most, if not all, of the length of balloon main body 16. The presence of a plurality of aligned cutters as shown and described allows the balloon to more easily bend, or flex, during insertion, or as the balloon traverses tortuous bodily passageways. Thus, the trackability of a balloon having the multiple cutters is enhanced, when compared to a balloon having a single elongated cutter. In addition, the lack of flexibility of a balloon having a single elongated cutter increases the risk of disengagement of the cutter as the balloon traverses these passageways.

As a further variation, the cutters need not be aligned in parallel fashion along a row. Rather, for example, some of the cutters can be arranged as shown, and others may be aligned at any angle to them, such as perpendicular. Furthermore, the cutters need not be arranged in parallel rows as illustrated in the figures. Rather, the cutters can be arranged in any one of an infinite number of configurations along the circumference of the balloon. However, for ease of manufacturing and use, and for versatility in cutting ability, the arrangement shown in the figures is preferred.

Figure 6:
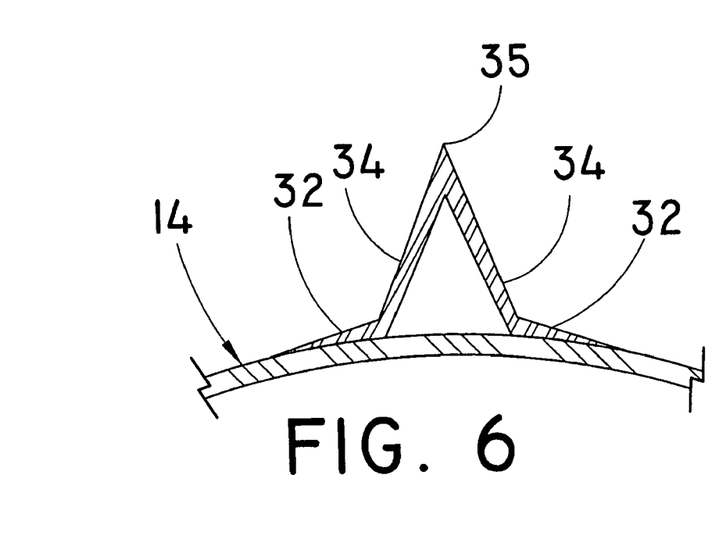
FIG. 6 is a sectional view of a cutter for the balloon catheter, taken along line 6-6 of FIG. 2.
Figure 7:
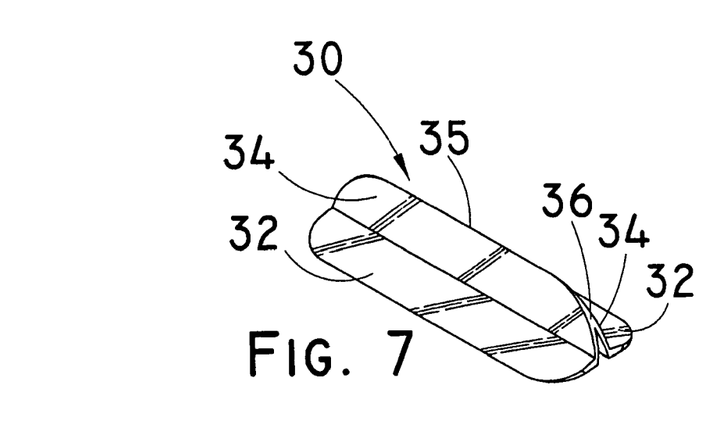
FIG. 7 is a perspective view of one form of a cutter, shown removed from the balloon.

The cutters 30 are best shown in FIGS. 6 and 7. Cutters 30 preferably include opposing base portions 32 and converging body portions 34. Body portions 34 converge to meet at sharp edge 35. The cutters may generally be formed by techniques well known in the art, such as by molding or extrusion. Preferably, the cutters are formed such that the corners or edges 36 are curved, as best shown in FIG. 7. This configuration eliminates the presence of sharp corners or edges, thereby minimizing the possibility of inadvertently cutting the artery during insertion.

The cutters 30 may be attached to balloon cylindrical body surface 16 by any well-known method utilized in the medical arts for joining components. Preferably, the cutters are bonded to the outer surface of balloon 14. Heat bonding is a particularly preferred technique that may be used for forming a strong bond between polymeric compositions. Heat bonding is a well-known technique, and those skilled in the art can readily determine appropriate conditions upon which a particular bonding operation may be carried out. One particularly preferred heat bonding technique is laser-welding of the cutter to the outer balloon surface. Other techniques suitable for a particular bonding operation include, but are not limited to, adhesive bonding and/or solvent bonding. When bonding techniques such as adhesive and/or solvent bonding are carried out, those skilled in the art will appreciate that only biologically compatible materials should be used. Other known attachment means may be used in place of, or in combination with, bonding. As another alternative, the cutters may be bonded or otherwise attached to the balloon during the process of forming the balloon. As still another alternative, balloon 14 can be formed with integral cutter portions 30.

As stated, the cutters 30 and the balloon 14 are formed from the same or a similar polymer in a preferred embodiment of the invention. When the same or similar polymers are utilized for the balloon and the cutters, the bonding of such polymers will normally result in a very favorable and strong seal therebetween. In addition, when the cutters are formed of the same or a similar polymer as the balloon, the cutters have the ability to expand as the balloon is expanded, i.e., during inflation of the balloon.

Although it is preferred to utilize the same or a similar polymer for the cutters and the balloon, it is not necessary to do so. Rather, any compositions for the respective cutters and balloon that are suitable for the intended purpose may be substituted, as long as the respective compositions are sufficiently compatible such that the cutters may be securely bonded or otherwise attached to the outer circumference of the balloon. Although preferred, it is not necessary that the cutter even be formed from a polymer, and other compositions, such as metals, alloys (including shape memory alloys), composites, etc., may be appropriate for a particular usage. Those skilled in the art may readily select an appropriate composition for a particular application in accordance with the teachings of the present invention.

In addition, although it is preferred to provide cutters 30 having opposing base portions 32 and converging edges 34 as shown in FIGS. 6 and 7, the cutters need not necessarily have this configuration. Rather, for example, at least some of cutters need only have a single base, with one or more walls leading from the base to a cutting edge. As a still further alternative, cutters 30 need not even have a base and/or a wall, and the cutting edge can be adhered directly to the balloon surface. Nevertheless, for ease of operation, securement of bonding, enhanced trackability or bendability, etc., it is preferred to utilize the cutter configuration shown in FIGS. 6 and 7.

Figure 4:
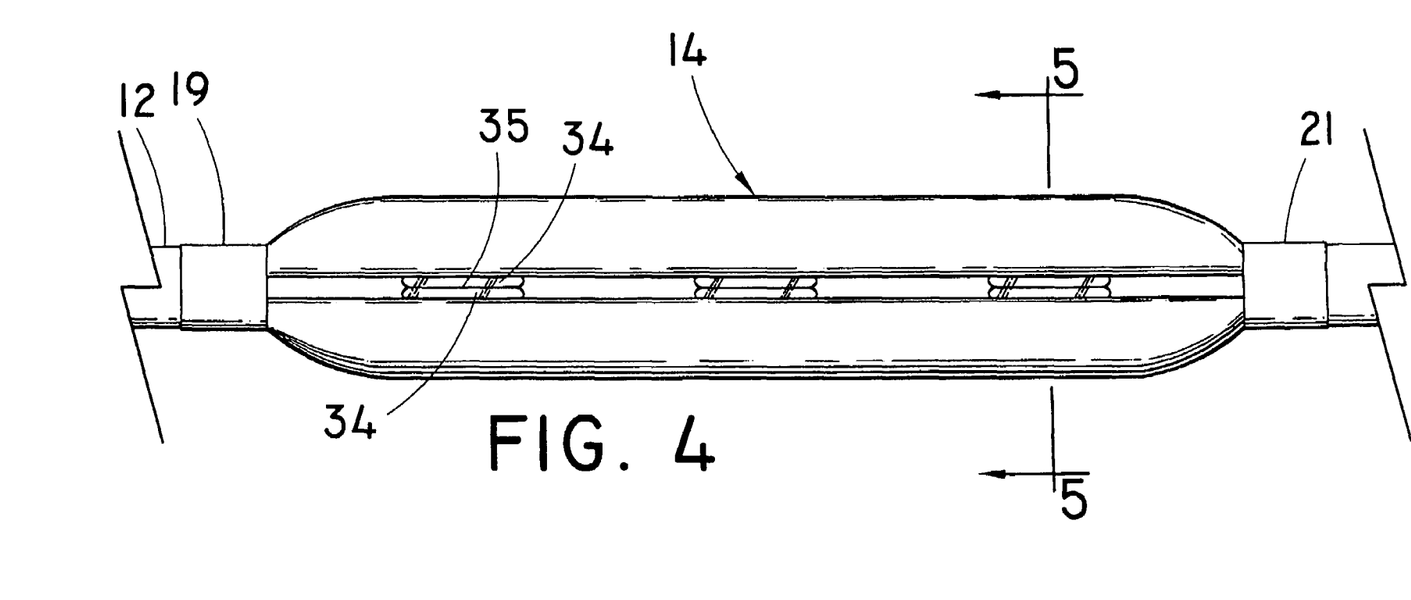
FIG. 4 is a side view of the balloon catheter portion of FIG. 1, showing the balloon in the uninflated condition.
Figure 5:
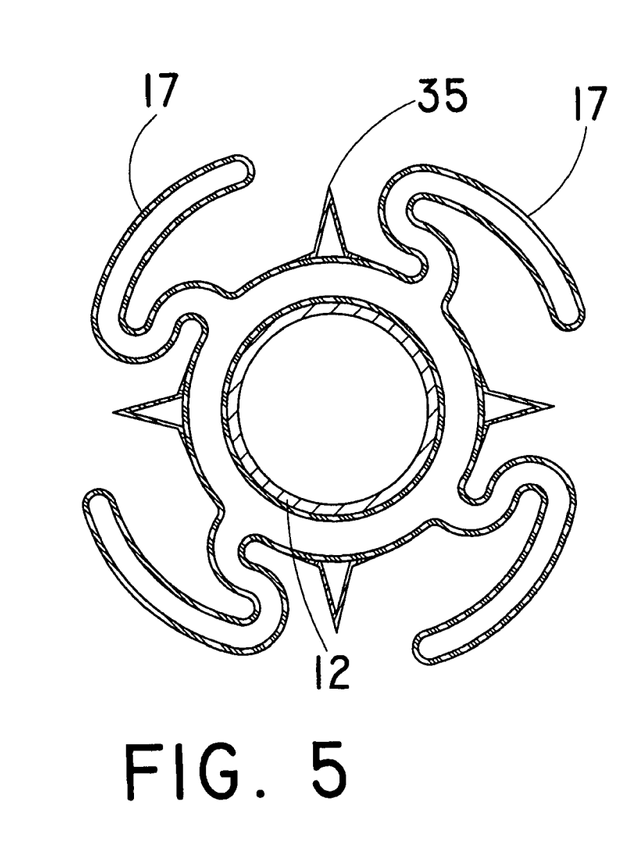
FIG. 5 is a sectional view of the catheter portion and uninflated balloon of FIG. 4, taken from line 5-5 of FIG. 4.

During use of balloon catheter assembly 10 in a balloon angioplasty procedure, the balloon 14 is initially wrapped around catheter shaft 12 in its uninflated condition, as illustrated in FIGS. 4 and 5. As shown in FIG. 5, sharp edges 35 of respective cutters 30 are shielded or otherwise covered by balloon folds 17. As a result, edges 35 are not exposed to the portions of the vessel that are traversed during the introduction of assembly 10 into the vessel. In addition, this arrangement protects medical personnel by reducing the possibility of inadvertent contact with a sharp cutter edge.

Those skilled in the art recognize that there are many ways in which a balloon catheter assembly may be introduced into a blood vessel, and accordingly, the inventive balloon catheter assembly 10 may be introduced in any of these well known ways. Preferably, the assembly is introduced over a wire guide that has previously been inserted into a vessel using, e.g., the well-known Seldinger percutaneous entry technique. A suitable guide catheter (not shown) may be introduced over the wire guide to provide a conduit for safe passage of the balloon catheter assembly to the site requiring treatment. Assembly 10 may then be advanced over the wire guide and through the guide catheter until the area of a vascular restriction, such as a hardened lesion, is encountered. The balloon portion of the assembly exits the distal end of the guide catheter and passes into the area of the restriction.

Proper position of the balloon, and thus the cutters, may be verified under a suitable imaging technique, such as x-ray fluoroscopy. In order to facilitate visualization, the catheter shaft may be provided with one or more radiopaque markers in conventional fashion. Although the markers may be spaced at any desired location along the shaft, it is preferred to position them on the portion of the shaft inside of the balloon. Following verification of proper placement, balloon 14 may be inflated by well-known means. Inflation of the balloon causes the sharp edge 35 of respective cutters 30 to engage and thereby break down the restriction. The balloon may be deflated and re-inflated one or more additional times if desired. The assembly may also be rotated prior to re-inflation such that additional segments of the restriction may be directly engaged by the cutters.

Following breakdown of the restriction, the balloon is deflated such that it returns to the general shape illustrated in FIG. 5. The balloon catheter assembly may then be retracted over the wire guide, through the guide catheter, and removed from the vessel.

It is therefore intended that the foregoing detailed description be regarded as illustrative rather than limiting, and that it be understood that it is the following claims, including all equivalents, that are intended to define the spirit and scope of this invention.

The invention claimed is:

1. A balloon catheter assembly, comprising:
    an elongate catheter shaft having a proximal portion and a distal portion;
    an inflatable balloon secured to said distal portion of said catheter shaft; and
    a plurality of cutters disposed along an outer surface of the balloon, said cutters comprising a pair of spaced base segments in fixed engagement with said balloon outer surface, said base segments of each cutter having an open space between said base segments along a circumference of said balloon such that a spacing between said base segments along the circumference of said balloon is variable, said cutters further including respective body portions that extend radially from each base segment and converge toward one another, said respective converging body portions configured and aligned to meet to define a cutting edge, said cutters being shielded by folds of the balloon when said balloon is in an uninflated condition, and being arranged and configured to facilitate breakdown of a vascular restriction when said balloon is in an inflated condition, said cutters being fixedly engaged with said outer surface of said balloon.

2. The balloon catheter assembly of claim 1, wherein at least some of said cutters are disposed in respective generally parallel longitudinal rows along said balloon outer surface.

3. The balloon catheter assembly of claim 2, wherein said cutters are disposed in at least three generally parallel longitudinal rows along said balloon outer surface.

4. The balloon catheter assembly of claim 3, wherein each row includes at least three longitudinally-aligned cutters.

5. The balloon catheter assembly of claim 4, wherein said cutters are substantially equally spaced along said row.

6. The balloon catheter assembly of claim 3, wherein said balloon comprises a polymer, said polymer selected from the group consisting of polyamides, polyethylene terephthalate, polyether block amides, and blends of the foregoing.

7. The balloon catheter assembly of claim 3, wherein said balloon comprises a noncompliant balloon having a generally cylindrical configuration upon inflation.

8. The balloon catheter assembly of claim 2, wherein said cutters are disposed in four generally parallel longitudinal rows along said balloon outer surface, said rows being spaced at substantially 90 degree intervals along said outer surface.

9. The balloon catheter assembly of claim 1, wherein said cutting edges have an elongated cutting surface and have a curved surface at an axial edge of said cutting surface.

10. The balloon catheter assembly of claim 1, wherein said elongate catheter has a lumen longitudinally extending therein, an interior space of said balloon being in fluid communication with said lumen for receiving an inflation fluid therefrom.

11. The balloon catheter assembly of claim 1, wherein said balloon is formed from a polymer, and said cutters are formed from the same polymer as the balloon, and wherein said cutters are heat bonded to said balloon outer surface.

12. The balloon catheter assembly of claim 1, wherein said balloon comprises a polymer selected from the group consisting of polyamides, polyethylene terephthalate, polyether block amides, and blends of the foregoing, and said cutter comprises a polymer capable of fixed engagement with the outer surface of said balloon by heat bonding, each of said cutter rows including at least three longitudinally-aligned cutters substantially equally spaced along said row.

13. A method for breaking down a restriction in a blood vessel of a patient, comprising:
providing a balloon catheter assembly for insertion into said vessel, said balloon catheter assembly comprising an elongate catheter shaft and an inflatable balloon secured to a distal portion of said catheter shaft, said balloon having a plurality of cutters fixedly disposed in respective generally parallel longitudinal rows along an outer surface of said balloon, said cutters including a base portion comprising a pair of opposing spaced base segments in fixed engagement with said balloon outer surface, said opposing spaced base segments of each cutter having an open space between said spaced base segments along a circumference of said balloon such that a distance between said spaced segments is variable as said balloon catheter assembly traverses said vessel, said cutters further including respective body portions that converge toward one another, said respective converging body portions configured and aligned to meet to define a cutting edge, said cutters being arranged in respective longitudinal rows along said balloon outer surface wherein each row comprises a plurality of said cutters, said cutters being shielded by folds of the balloon when said balloon is in an uninflated condition, and being arranged and configured to facilitate a breakdown of said restriction when said balloon is in an inflated condition;
inserting the distal end of the balloon catheter assembly into said vessel, and advancing the assembly in the vessel with the balloon in an uninflated condition until said uninflated balloon reaches said restriction;
inflating the balloon such that said cutters penetrate said restriction;
deflating said balloon; and
withdrawing said balloon catheter assembly from said vessel.

14. The method of claim 13, wherein said cutters are disposed in at least three generally parallel longitudinal rows along said balloon outer surface, each of said rows comprising at least three cutters, said rows being spaced at substantially equal intervals along said outer surface.

15. The method of claim 13, wherein said inflating and deflating steps are repeated at least one additional time prior to withdrawing the balloon catheter assembly from the vessel.

16. The method of claim 15, wherein said assembly is rotated prior to said at least one additional step of inflating and deflating.

17. The method of claim 13, wherein said assembly is inserted into the vessel utilizing the Seldinger technique.

18. The method of claim 13, wherein said balloon and said cutters are formed from a polymer, and said cutters are heat bonded to said balloon outer surface.

19. A balloon catheter assembly for breaking down a restriction in a body vessel of a patient, comprising:
an elongate catheter shaft having a proximal portion and a distal portion;
an inflatable polymeric balloon secured to said distal portion of said catheter shaft; and
a plurality of cutters disposed along an outer surface of the balloon, said cutters being arranged in at least three generally parallel longitudinal rows along said balloon outer surface, each row including a plurality of longitudinally-aligned cutters, each cutter including a base portion comprising a pair of spaced base segments affixed to said balloon outer surface, said base segments of each cutter having an open space between said base segments along a circumference of said balloon outer surface such that a spacing between said base segments is variable as said balloon catheter assembly traverses said vessel, and further including respective body portions that extend radially from each base segment and converge toward one another, said respective converging body portions configured and aligned to meet to define an elongated cutting edge and a curved surface at each axial end of said cutting edge, said cutters being shielded by folds of the balloon when said balloon is in an uninflated condition, and being arranged and configured to facilitate breakdown of said restriction when said balloon is in an inflated condition, said cutters and balloon being formed from the same polymer, and wherein said cutters are heat bonded to said balloon outer surface.

* * * * *